United States Patent [19]

Boyer et al.

[11] Patent Number: 5,171,263

[45] Date of Patent: Dec. 15, 1992

[54] CARDIAC VALVE WITH FLAPS PIVOTING ON BALLS

[75] Inventors: Robert Boyer, Pierrelatte; René Ranc, Grenoble; René, deceased Stefani, Meylan, all of France, represented by Noelle Stefani

[73] Assignees: Commissariat A L'Energie Atomique, Paris; Cogema -Compagnie Generale Des Matieres Nucleaires, Veilzy Villacoublay, both of France

[21] Appl. No.: 626,546

[22] Filed: Dec. 12, 1990

[30] Foreign Application Priority Data

Dec. 20, 1989 [FR] France ................. 89 16900

[51] Int. Cl.$^5$ ............................................. A61F 2/24
[52] U.S. Cl. ........................................ 623/2; 137/527; 137/512.1
[58] Field of Search ............ 623/2; 137/527, 512.1

[56] References Cited

U.S. PATENT DOCUMENTS

| | | | |
|---|---|---|---|
| 3,953,898 | 5/1976 | Bloch | 623/2 |
| 4,078,268 | 3/1978 | Possis | 623/2 |
| 4,159,543 | 7/1979 | Carpentier | 623/2 |
| 4,308,624 | 1/1982 | Klawitter | 623/2 |
| 4,446,577 | 5/1984 | Meyer et al. | 623/2 |
| 4,872,875 | 10/1989 | Hwang | 623/2 |

FOREIGN PATENT DOCUMENTS

| | | |
|---|---|---|
| 678968 | 9/1966 | Belgium . |
| 0039217 | 11/1981 | European Pat. Off. . |
| 0091746 | 10/1983 | European Pat. Off. . |

OTHER PUBLICATIONS

RCA Technical Notes, No. 1151, May 24, 1976, pp. 1-4; J. W. Knoll: "Prosthetic heart valve"-p. 2, lines 5-17; FIG. 1.

*Primary Examiner*—Ronald Frinks
*Attorney, Agent, or Firm*—Oblon, Spivak, McClelland, Maier & Neustadt

[57] ABSTRACT

A cardiac valve comprises a ring, one or more flaps, the pivoting axis of the latter including two balls partly extending into a ring cavity and a conical flap cavity. This arrangement improves the life of the valve by reducing wear, stresses, friction and facilitates the assembly thereof if the ring is constituted by two concentric members and if the ring cavity extends on either side of the inner member. The invention more particularly applies to artificial valves installed in the heart in place of defective natural valves.

5 Claims, 2 Drawing Sheets

CARDIAC VALVE WITH FLAPS PIVOTING ON BALLS

BACKGROUND OF THE INVENTION

1. Field of the Invention

The invention relates to a cardiac valve with flaps pivoting on balls.

Use is at present made of valves installed on the cardiac muscle making it possible to replace defective natural valves. In general terms said valves comprise a ring for holding the valve on the muscle and which carries an articulation means for one or more members which are displaced under the action of the blood flow between an opening position corresponding to the desired outflow direction and a closed position corresponding to the reverse direction. The main qualities needed for such valves are a good sealing in the closed position, the creation of a limited pressure drop in the opening direction, slow wear and an inability to lead to coagulation and thromboses.

2. Discussion of the Related Art

Existing valves only make it possible to inadequately achieve these objectives. Among the existing systems, reference can firstly be made to valves in which the flap is displaced by alternative translation. The connection system to the ring is then a fitting constituted by an appropriately curved rod and the flap can be constituted by a ball or by a disk. These valves create a significant pressure drop in the opening direction, because the member continues to disturb the blood flow and they are also subject to friction and wear. For this reason valves have been developed, which have one or more flaps connected to the ring by pivots materializing off centred rotation axes, in such a way that the pressure of the blood is adequate for pivoting them. However, wear still exists, as do stress concentrations on the pivots and the adjacent parts of the flaps and ring. Moreover, it is far from easy to assemble such valves, because it is necessary to create elastic deformations in order to permit the insertion of the pivots into a cavity of the flap or the ring. Such an operation may lead to a deterioration of the coating of the coagulation-preventing materials, such as pyrocarbon, which normally cover the substrate material of the different parts.

SUMMARY OF THE INVENTION

Therefore the object of the present invention is to obviate these disadvantages and provide a cardiac valve in which friction and wear are reduced and in which assembly and operation are easy.

This valve in general terms comprises a ring, at least one flap surrounded by the ring, pivoting means making it possible to pivot the flaps with respect to the ring, abutment means for the flaps defining a pivoting travel for the flaps between an open position and a closed position of the valve and characterized in that the pivoting means are constituted by two balls for each flap and in that the ring and the flaps are provided with cavities, each ball being partly located in a ring cavity and partly in a flap cavity. The ring is also constituted by an inner member and an outer member, which are concentric and contiguous the ring cavities being carried by the inner member exclusively and radially traverse the inner member.

Preferably, the cavities of the flaps have a conical bottom.

BRIEF DESCRIPTION OF THE DRAWINGS

The invention is described in greater detail hereinafter relative to non-limitative embodiments and the attached drawings, wherein show.

DESCRIPTION OF THE PREFERRED EMBODIMENTS

Figure 1:
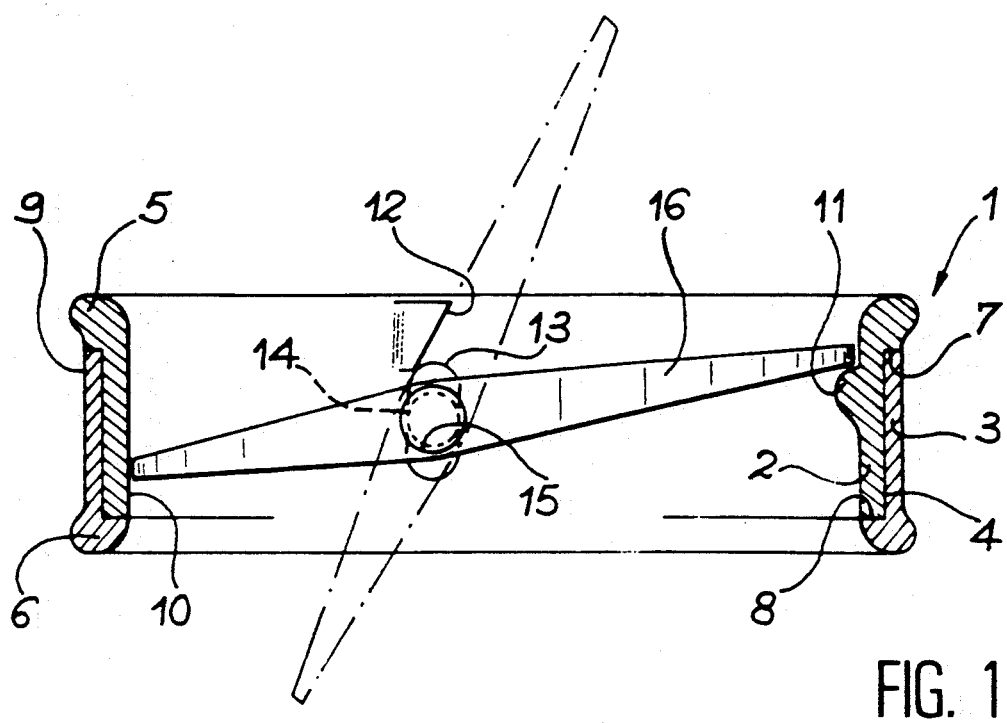
FIGS. 1 and 2 show an embodiment of the invention with a single flap in longitudinal section and in plan view.
Figure 2:
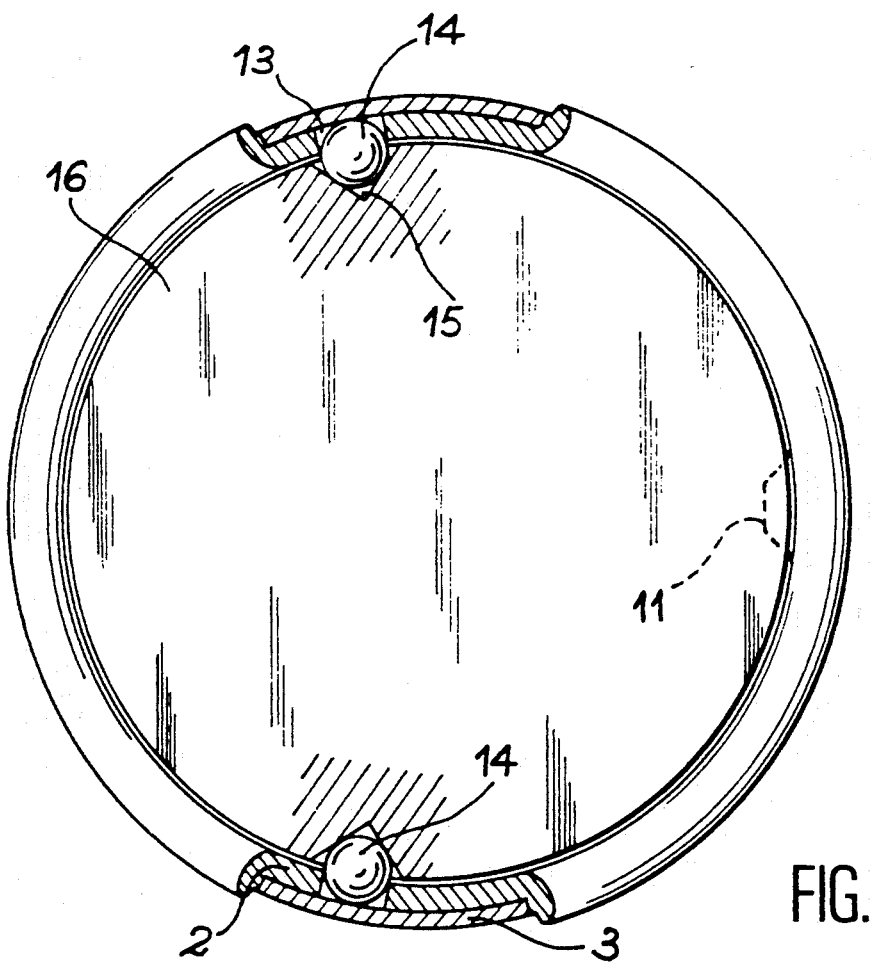

Thus, the valve of FIGS. 1 and 2 has a ring 1 constituted by an inner member 2 and an outer member 3, which are concentric and contiguous by a cylindrical connecting surface 4. Each of the inner 2 and outer 3 members comprises a circumferential flange oriented towards the outside and respectively designated 5 and 6, each of the flanges being terminated by a surface, respectively 7 and 8, against which abuts and end bearing of the other member. It can be seen that it is possible to ensure the assembly of the ring 1 by firstly placing the inner and outer members 2, 3 respectively in an extension of one another and then making them slide in one another until abutment occurs at the surfaces 7 and 8. Following the fitting, the connection can be made irreversible by means of a weld or any other equivalent means on the joint lines. The flanges 5 and 6 are then located at the longitudinal ends of the ring 1 and the outer face 9 is in depression between them.

The outer member 3 is smooth and continuous, i.e. perfectly cylindrical, outside the flange 6. However, the inner member 2 is provided on its inner face 10 with a closed position abutment 11 and an open position abutment 12 for the flap, as well as two ring cavities 13 traversing the same and whose orientation is radial. However, the two cavities 13 are not diametrically opposite on the inner member 2.

Each of the ring cavities 13 receives approximately half a ball 14, whereof the remainder is largely contained in a conical flap cavity 15, which has a disk shape on the flap 16. As can be seen in FIG. 2, the radial clearance between the flap 16 and the inner member 2 is small and the circumferential, radial clearnace between the balls 14 in the ring cavities 13 and the flap cavities 15 respectively is virtually non-existant. The ring cavities 13 can have an oblong section, which is more extensive in the axial direction of the ring 1, which allows clearances of the balls 14 and the flaps 16 of a few tenths of a millimeter or a few millimeters in said direction. The outer member 3 encloses the cavities 13, 15 to prevent the balls 14 from escaping. The object of this arrangement is to prevent coagulation by ensuring a significant movement of the constituent parts of the valve close to the pivoting axis. French Pat. 2 331 997 describes an identical idea in a valve, where the pivots are in one piece with the ring or the flap.

The advantages of the invention will now be described. Firstly, the construction of the ring 1 with the aid of two contiguous members 2 and 3, whereof the first is provided with ring cavities 13, makes it possible to carry out assembly by positioning the flap 16 relative to the inner member 2, then introducing the balls 14 into the ring and flap cavities 13, 15 and finally by fitting the two rings. Significant deformations are not created. Moreover, the spherical shape of the balls 14 limits the friction surfaces and therefore the magnitude of the friction, which obviates supplementary stressing of the cardiac muscle. Supplementary advantages of the spherical shape are a reduction in the stress concentrations and a uniform distribution of wear as a result of the inevitable rotations of the balls 14 in their cavities, according to the random movements independent of the rotary movements of the flap 16, which greatly increases the operating life of such valves. Finally, as there are separate pivots for the ring 1 and the flap 16, supplementary possibilities are provided regarding the choice and combination of materials. As a function of the possibly different materials for the ring 1 and the flap 16, it is possible to choose an optimum material from the wear and friction standpoint for the balls 14.

Figure 3:
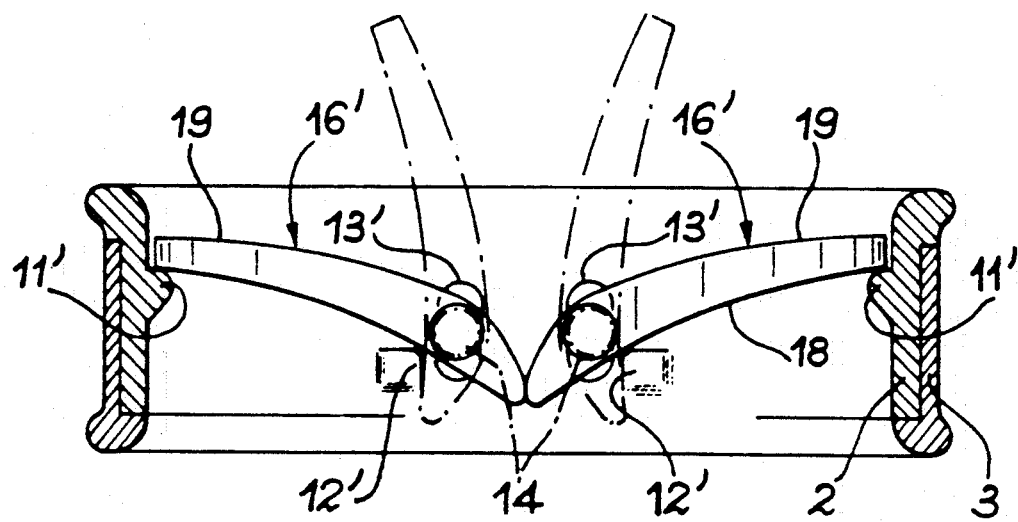
FIGS. 3 and 4 show similar views of another embodiment of the invention with a double flap.
Figure 4:
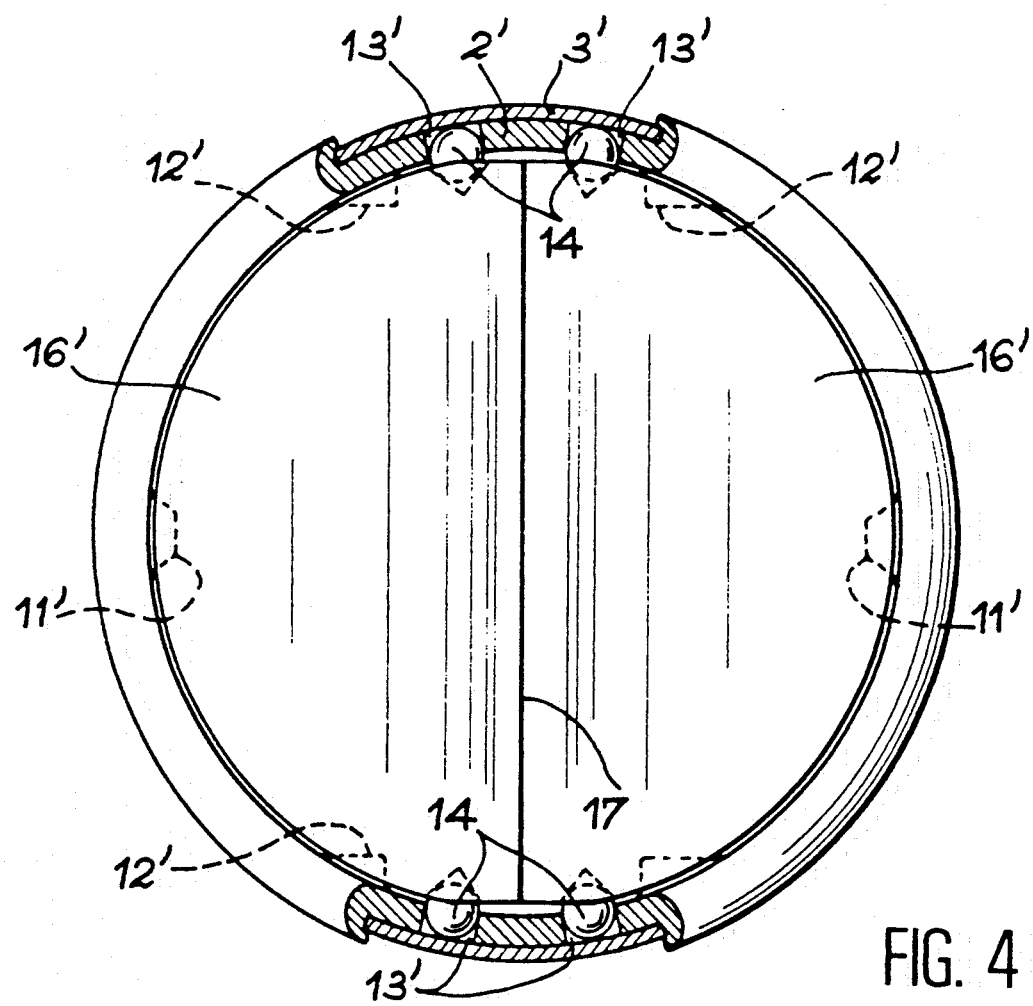

FIGS. 3 and 4 show another embodiment, in which the single flap 16 is replaced by two generally semicircular flaps 16'. It is then necessary to modify the inner member, now designated 2'. It also has four ring cavities 13' for the partial reception of the four balls 14. The overall arrangement is such that each ball 14 is, following the circumference of the inner member 2, close to a second ball and diametrically opposite to a third ball, the second and third balls being used to pivot one of the flaps 16'. Thus, the flap 16' pivot about parallel axes which are close to one another. In the closed position, sealing is maintained, because the flaps 16' are contiguous on a central joint line 17. In the open position, blood flows symmetrically into three adjacent channels defined by the ring 1 and the flap 16' and its outflow is better than with the preceding valve. This advantage is reinforced if the flaps 16' are curved and have a concave upstream face 18 and a convex downstream face 19, whereas the preceding flap 16 was planar tapering or moving away from the pivoting axis.

It is also necessary to provide at least one closed position abutment 11' and open position abutment 12' for each of the flaps 16'. Apart from this, all the constructional arrangements applicable to the first embodiment can be used here.

We claim:

1. A cardiac valve comprising:
   a ring, said ring comprising an inner member and an outer member which are concentric and contiguous;
   at least one flap surrounded by the ring;
   pivoting means for permitting a pivoting of the at least one flap with respect to the ring; and
   abutment means for the at least one flap, said abutment means defining a pivoting travel of the at least one flap between an open position and a closed position of the valve;
   wherein;
   the pivoting means comprise two balls for said at least one flap;
   said ring comprises ring cavities which are exclusively carried by the inner member and radially traverse the inner member;
   said at least one flap comprises flap cavities;
   each one of said two balls is partly located in a ring cavity and partly located in a flap cavity such that each one of said two balls are freely rotatable in said cavities; and
   said outer member encloses the cavities for preventing the balls from escaping.

2. The cardiac valve according to claim 1, characterized in that certain of the ring cavities have an elongated section permitting displacements in translation of the at least one flap.

3. The cardiac valve according to claim 1, characterized in that the flap cavities have a conical bottom.

4. The cardiac valve according to claim 1, characterized by a single flap.

5. The cardiac valve according to claim 1, characterized by two flaps pivoting about parallel axes.

* * * * *